(12) United States Patent
Lim et al.

(10) Patent No.: US 9,902,977 B2
(45) Date of Patent: Feb. 27, 2018

(54) PROCESS OF PRODUCING BIOENERGY WITH LOW CARBON DIOXIDE EMISSIONS AND ZERO-WASTE OF BIOMASS

(71) Applicants: Industry Academic Cooperation Foundation, Daegu University, Gyeongsan-si, Gyeongsangbuk-do (KR); Myongji University Industry and Academia Cooperation Foundation, Yongin-si, Gyeonggi-do (KR); KOREA INSTITUTE OF SCIENCE AND TECHNOLOGY, Seoul (KR); INDUSTRY ACADEMIC COOPERATION FOUNDATION KEIMYUNG UNIVERSITY, Daegu (KR)

(72) Inventors: Kwang-Hee Lim, Daegu (KR); Kisay Lee, Yongin-si (KR); Young-Soon Um, Seoul (KR); Min-Woo Lee, Daegu (KR)

(73) Assignees: INDUSTRY ACADEMIC COOPERATION FOUNDATION. DAEGU UNIVERSITY, Gyeongsan-si (KR); MYONGJI UNIVERSITY INDUSTRY AND ACADEMIA COOPERATION FOUNDATION, Yongin-si (KR); KOREA INSTITUTE OF SCIENCE AND TECHNOLOGY, Seoul (KR); INDUSTRY ACADEMIC COOPERATION FOUNDATION KEIMYUNG UNIVERSITY, Daegu (KR)

( * ) Notice: Subject to any disclaimer, the term of this patent is extended or adjusted under 35 U.S.C. 154(b) by 65 days.

(21) Appl. No.: 14/468,457

(22) Filed: Aug. 26, 2014

(65) Prior Publication Data
US 2015/0064761 A1    Mar. 5, 2015

(30) Foreign Application Priority Data

Aug. 27, 2013 (KR) .................. 10-2013-0101770
May 26, 2014 (KR) .................. 10-2014-0062683

(51) Int. Cl.
| | |
|---|---|
| C12P 7/16 | (2006.01) |
| C12P 7/06 | (2006.01) |
| C12N 1/12 | (2006.01) |
| C12P 5/02 | (2006.01) |
| C12P 7/10 | (2006.01) |
| C12P 7/64 | (2006.01) |

(52) U.S. Cl.
CPC .................. *C12P 7/16* (2013.01); *C12N 1/12* (2013.01); *C12P 5/023* (2013.01); *C12P 7/10* (2013.01); *C12P 7/6463* (2013.01); *C12P 2203/00* (2013.01); *Y02E 50/10* (2013.01); *Y02E 50/16* (2013.01); *Y02E 50/17* (2013.01); *Y02E 50/343* (2013.01)

(58) Field of Classification Search
None
See application file for complete search history.

(56) References Cited

U.S. PATENT DOCUMENTS

| | | | | |
|---|---|---|---|---|
| 2009/0031615 | A1* | 2/2009 | Joshi .................. | C10G 2/32 44/307 |
| 2009/0227003 | A1* | 9/2009 | Blotsky ................ | C12M 21/02 435/257.1 |
| 2009/0321349 | A1* | 12/2009 | Offerman .............. | C10G 2/32 210/603 |

(Continued)

OTHER PUBLICATIONS

Patil et al., Towards Sustainable Production of Biofuels from Microalgae, Int. J. Mol. Sci. 2008, 9, 1188-1195.*
Singh et al., A critical review of biochemical conversion, sustainability and life cycle assessment of algal biofuels, Applied Energy 88 (2011) 3548-3555.*
Subhadra, Sustainability of algal biofuel production using integrated renewable energy park (IREP) and algal biorefinery approach, Energy Policy, 38 (2010) 5892-5901.*
Ventura et al., Life cycle analyses of CO2, energy, and cost for four different routes of microalgal bioenergy conversion, Bioresource Technology vol. 137, Jun. 2013, pp. 302-310.*

(Continued)

*Primary Examiner* — Karen Cochrane Carlson
*Assistant Examiner* — Jennifer M. H. Tichy
(74) *Attorney, Agent, or Firm* — Birch, Stewart, Kolasch & Birch, LLP

(57) ABSTRACT

Disclosed herein is a bioenergy production system with reduced carbon dioxide emissions and process wastes; including a process for producing a bioalcohol and a biogas by subjecting a biomass, such as: herbaceous and woody plants, fruit pulp, freshwater and sea algae, grains, aerobic and anaerobic sludge, saccharides, polyols and carbohydrates, to a combined process of a biosaccharification/alcohol fermentation, including a biomass pretreatment process; and a process for producing a methane biogas with a reduced level of carbon dioxide and hydrogen sulfide, via an algae cultivation process with a view to purifying the carbon dioxide and hydrogen sulfide contained in the biogas; wherein, when the algae to be cultivated is microalgae, biodiesel is produced by subjecting the harvested microalgae to a biodiesel manufacturing process while recycling the glycerol and the saccharide-containing waste produced as byproducts to the biosaccharification/alcohol fermentation process, and when the algae to be cultivated is macroalgae the harvested macroalgae is recycled to the biosaccharification/alcohol fermentation process. The method of the present invention is effective in reducing carbon dioxide emissions, a representative green house gas contributing to the global warming, and also in optimizing a zero-waste bioenergy production system.

19 Claims, 6 Drawing Sheets

(56) References Cited

U.S. PATENT DOCUMENTS

| | | | | |
|---|---|---|---|---|
| 2011/0003357 A1* | 1/2011 | Barclay | ............... | A01G 33/00 |
| | | | | 435/167 |
| 2011/0091954 A1* | 4/2011 | Chen | ............... | A01H 13/00 |
| | | | | 435/168 |
| 2011/0201063 A1* | 8/2011 | Mitropoulos | ......... | C12M 21/02 |
| | | | | 435/134 |
| 2011/0287497 A1* | 11/2011 | Holtzapple | ............. | C12P 5/00 |
| | | | | 435/134 |
| 2013/0143290 A1* | 6/2013 | Narendranath | .......... | C12P 7/10 |
| | | | | 435/165 |

OTHER PUBLICATIONS

Dai et al., Broth Recycling in Liquid Cultivation of Nostoc Flagelliforme Cells, Information Tech. and Agricultural Eng., AISC 134, (2012), pp. 39-48.*

Extension, Waste Management in Biodiesel Production, Mar. 26, 2012, Available Online at: articles.extension.org/pages/27660/waste-management-in-biodiesel-production.*

Yu et al., "2012 KSIEC Fall Meeting" Academic poster published on Nov. 2, 2012 by the Inventor Lee, Kisay.

\* cited by examiner

FIG. 1

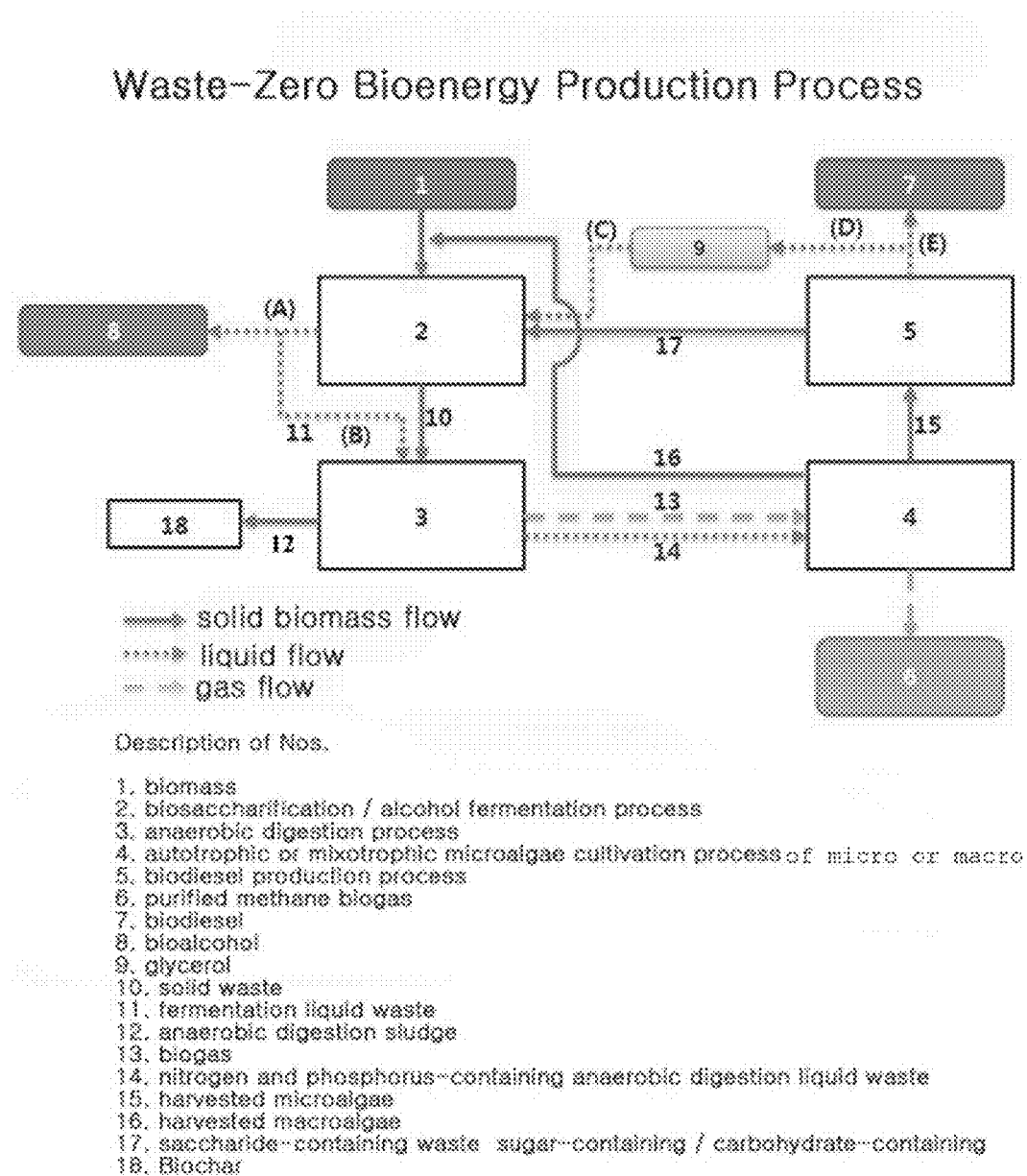

→ solid biomass flow
⋯▶ liquid flow
— — gas flow

Description of Nos.

1. biomass
2. biosaccharification / alcohol fermentation process
3. anaerobic digestion process
4. autotrophic or mixotrophic microalgae cultivation process of micro or macro algae
5. biodiesel production process
6. purified methane biogas
7. biodiesel
8. bioalcohol
9. glycerol
10. solid waste
11. fermentation liquid waste
12. anaerobic digestion sludge
13. biogas
14. nitrogen and phosphorus-containing anaerobic digestion liquid waste
15. harvested microalgae
16. harvested macroalgae
17. saccharide-containing waste  sugar-containing / carbohydrate-containing
18. Biochar

PROCESS OF PRODUCING BIOENERGY WITH LOW CARBON DIOXIDE EMISSIONS AND ZERO-WASTE OF BIOMASS

BACKGROUND OF THE INVENTION

1. Field of the Invention

The present invention relates, in general, to a method for producing bioenergy with reduced discharge of carbon dioxide and process-related waste and, more particularly, to a method for producing zero-waste bioenergy with reduced emissions of carbon dioxide, i.e.: a representative greenhouse gas contributing to global warming; and maximized biomass treatment efficiency and bioenergy productivity.

2. Description of the Related Art

As well known in the art, examples of representative bioenergy sources may include fuels such as bioethanol and biodiesel. Until recently, bioethanol has been directly produced using yeast microorganisms such as *Saccharomyces cerevisiae* and *Pichia stipites*, which produce ethanol from saccharides such as glucose and xylose; or a microorganism such as enterobacter which produces ethanol from glycerol (Kim, J. H. et al., Ethanol production by simultaneous saccharification and fermentation with yeast *Saccharomyces cerevisiae*, The Korea Society for Energy Engineering, 10, 299-311, 2008).

Recently, biobutanol has been actively studied as a next generation fuel along with bioethanol, and has been highlighted as the next generation fuel due to its lack of engine corrosion and high miscibility with gasoline at high concentration (Bahl, H. W. et al., continuous production of acetone and butanol by *Clostridium acetobutylicum* in a two-stage phosphate limited chemostat, European Journal of Applied Microbiology and Biotechnology, 15, 201-205, 1982).

Biobutanol may be produced by butanol-producing microorganisms such as *Clostridium acetobutylicum*, *Clostridium beijerinckii*, and *Clostridium saccharobutylicum*; or directly from *Clostridium pasteurianum*, etc., which produce butanol from glycerol, and which also produce 1,3-propanediol (Ezeji, T. N. et al., Butanol production from agricultural residues: impact of degradation products on *Clostridium beijerinckii* growth and Butanol fermentation, Biotechnology and Bioengineering, 97, 1460-1469, 2007).

The amount of the global bioethanol production, which had reached 46 billion liters in 2005, has been continuously increasing (Jae, J. K. et al., A review on thermochemical pretreatment in Lignocellulosic bioethanol production, Korea Organic Resource Recycling Association, 16, 79-88, 2008). However, since the resulting production of the fermentation liquid waste, corresponding to about 6-10 times that of the bioethanol production, is a source of environmental pollution at the time of its release, the technology of treating the fermentation liquid waste will soon become a core, essential technology in the bioethanol production process.

Meanwhile, an anaerobic digestion process is a process utilizing a series of sequential microbial reactions where organic wastes are decomposed under anaerobic conditions, and a biogas containing methane and carbon dioxide is produced in the final step. In particular, since the advent of methane, a major component of a biogas, is a suitable energy source, the anaerobic digestion process has been widely used in energy production as well as in treating: excess sludge generated in sewage treatment plants, various kinds of byproducts generated in the food industry, high concentration organic wastewater, etc. Biogas refers to a gas generated during the fermentation/decomposition of organic waste under anaerobic conditions, including anaerobic digestion gas (ADG) and landfill gas (LFG). The anaerobic digestion gas refers to a gas generated during the anaerobic digestion process of organic materials such as food waste, livestock manure, and sewage sludge; and a landfill gas refers to a gas generated in landfill sites.

Biogas typically consists in $CH_4$ (40-60%), $CO_2$ (30-45%), $H_2S$ (0.1-5%), $N_2$ (2-5%), and $O_2$ (0.1-1%) as major components, along with a trace amount of other components including: CO, $H_2$, $NH_3$, mercaptan, and VOCs. In particular, the representative biogas components of $CH_4$ may be used as energy sources for co-generation plants, gas boilers, heating and cooling systems, heat pumps, etc. The calorific value of pure methane gas is about 9,000 kcal/m$^3$ and that of unpurified biogas is about 5,000-7,000 kcal/m$^3$. Accordingly, biogas has been highlighted as a major source of substitute energy due to recent high oil prices with the corresponding increasing fossil-fuel prices.

In the present invention, microalgae may refer to all single-celled and multi-celled microorganisms which belong to prokaryotic and eukaryotic algae, and cyanobacteria. Here, the term microalgae is further sub-divided into autotrophic-, heterotrophic-, and mixotrophic algae.

Autotrophic microalgae perform a so-called autotrophic energy metabolism when $CO_2$ is present as a carbon source during cultivation; during which $CO_2$ is reduced to carbohydrates, e.g.: starch in green algae and glycogen in blue-green algae; thereby being converted into an algal biomass as.

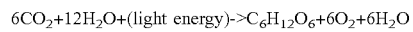
$$6CO_2+12H_2O+(\text{light energy})\rightarrow C_6H_{12}O_6+6O_2+6H_2O$$

Additionally, autotrophic microalgae, unlike the heterotrophic bacteria in conventional biological processes or in biofilers, can store energy in biomass via taking up $CO_2$ from biogas and $CO_2$-dissolved inorganic carbons without supplying additional carbon source. Therefore, the increase in microalgal biomass becomes final product of $CO_2$ elimination. In contrast, heterotrophic microalgae may be cultivated in stirred biological reactors or fermenters using organic carbon substrate, such as glucose, as a carbon source. Mixotrophic microalgae can perform both autotrophic and heterotrophic energy metabolism for growth.

Furthermore, when the microalgal biomass which is produced during the removal of $CO_2$ from biogas has a higher triglyceride content than that of other microorganisms, the microalgal biomass may be used as a feedstock for producing biodiesel. When microalgae is cultivated at high concentration, the resulting oil yield per unit area will be high compared to other crops and biomass can be produced at a faster rate than the general oil-producing crops. The doubling time of microalgae during exponential growth under optimal environment is a few hours at the shortest and within 2 or 3 days at the longest. Since microalgae can be cultivated in indoor bioreactors instead of outdoors, the production yield and productivity of microalgae can be improved via cultivation engineering. Accordingly, in a smaller country like South Korea where acquiring large cultivation area is difficult and weather condition is not optimal for biodiesel-producing crops; it is necessary to produce biodiesel from microalgle biomass in an indoor, intensive, high-density cultivation facility.

Furthermore, biodiesel in the form of fatty acid alkyl ester is produced through extracting fats/oil from cultivated algae via physical, chemical, and biological methods; and then carrying out trans-esterification of the extracted fats/oil.

Therefore, fatty acid methyl ester (FAME) is produced as biodiesel when methanol is used for the reaction as below.

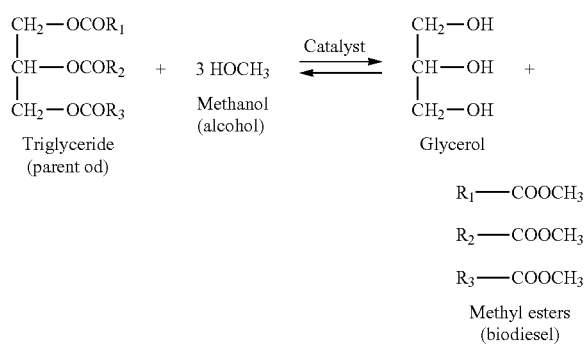

Bioenergy, being 'carbon neutral', can contribute to delaying and preventing global warming by reducing carbon dioxide emissions, compared to the conventional petroleum energy. Biosaccharification/ethanol fermentation, biosaccharification/butanol fermentation and biodiesel production are well-known bioenergy production processes.

Unlike other renewable energies, bioenergy in the liquid form like bioethanol and biodiesel can be mainly used as transportation fuel. energy as is the case with bioethanol and biodiesel.

As for the raw materials for producing bioenergy, starch such as edible corn and vegetable oil have been used as the first generation of biomass for producing bioethanol and biodiesel, respectively. As the second generation biomass, inedible fruit pulp, herbaceous plants, macroalgae, etc., have been used as raw materials for producing bioethanol, and also inedible freshwater or marine microalgae, waste vegetable oil or inedible vegetable oil such as rapeseed oil have been used. Recently, biomass such as woody plant and aerobic/anaerobic sludge has been spotlighted.

In South Korea, it is not possible to stably supply biomass. In the present invention, macroalgae such as *Sargassum, Gracilaria, Prymnesium parvum, Euglena gracilis, Gelidium amansii, Laminaria*, etc., may be used. However, under the current coastal conditions of South Korea, cultivating macroalgae for their continuous and stable supply is not easy. Additionally, the rape flower cultivation as a raw material for producing rapeseed oil has been reported uneconomical in South Korea. Furthermore, the lignocellulosic biomass has been mainly obtained from the 'forest tending' project performed two or three times annually or sawdust, and the transportation cost from biomass collection to users is considerably high as compared with other renewable energy sources.

SUMMARY OF THE INVENTION

The objective of the present invention is to improve biomass treatment efficiency and bioenergy productivity during the bioenergy production process, thereby reducing bioenergy production cost; wherein the transportation cost associated with the biomass collection accounts for a large portion of the production cost.

Another objective of the present invention is to improve bioenergy productivity by reducing the emissions of carbon dioxide generated during the bioenergy production process in order to prevent global warming.

A further objective of the present invention is to provide a novel use for glycerol, which is generated in large amounts as a byproduct in biodiesel production processes.

In order to accomplish the above objects, the present invention provides a method for producing bioenergy with maximized biomass treatment efficiency and bioenergy productivity via zero-discharge or minimized release of process waste resulting from the bioenergy production process of the present invention, including: producing bioalcohol from biomass via biosaccharification/alcohol fermentation; producing biogas via an anaerobic digestion of both solid byproducts generated from bioalcohol production process and liquid wastes generated during the bioalcohol purification; removing carbon dioxide, which is contained in the biogas, via algal photosynthesis so as to purify the biogas into a methane biogas and to produce biodiesel or bioalcohol from the algal biomass harvested via algal photosynthesis.

In order to accomplish the above objects, the present invention also provides a method to remove carbon dioxide contained in the biogas through purifying the biogas into a methane biogas by fixing carbon dioxide via algal photosynthesis thereby converting it into a carbon-neutral biomass, instead of using physic-chemical carbon capture storage (CCS) methods like adsorption/absorption which releases carbon dioxide into the atmosphere during regeneration.

The objects of the present invention described above can be achieved by the bioenergy production process capable of improving the cost-effectiveness of biodiesel production due to the development of a novel method of utilizing glycerol waste by supplying the high glycerol content waste generated during the biodiesel production process into an algal cultivation liquid of a heterotrophic algae cultivation process; or recycling it into the bioalcohol saccharification/fermentation process and utilizing it as a biomass raw material for producing bioalcohol.

ADVANTAGE OF THE INVENTION

The present invention has the advantages of providing a method to maximize the biomass treatment efficiency and bioenergy productivity due to a minimized-waste or waste-free production process, in addition to reducing the emissions of carbon dioxide, a greenhouse gas, thereby delaying or preventing global warming.

Furthermore, the present invention provides a method to enhance the cost-effectiveness of biodiesel production via the development of a novel usage of glycerol waste by supplying a high glycerol content waste produced during the biodiesel production process into an algae cultivation liquid of the heterotrophic algae cultivation process, or recycling it into the biosaccharification/alcohol fermentation process to utilize it as a biomass raw material for producing bioalcohol n, i.e.: producing a biofuel using a biodiesel waste, thereby enabling an eco-friendly production of a biofuel.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a diagram showing a waste-free or zero-waste bioenergy production method exclusive of a heterotrophic microalgae cultivation process;

DESCRIPTION OF THE PREFERRED EMBODIMENTS

Figure 2:
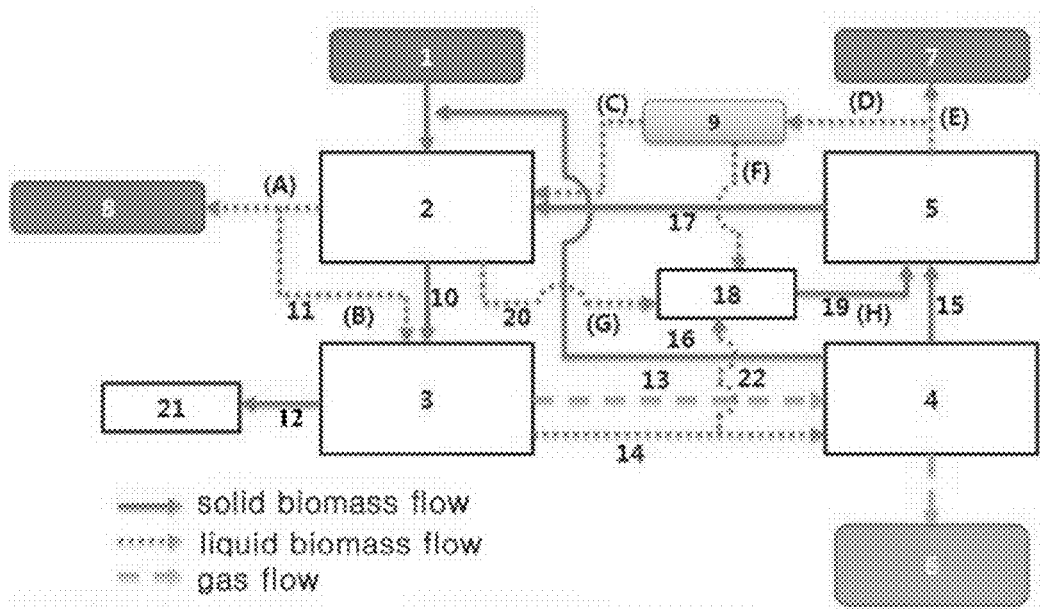
FIG. 2 is a diagram showing a waste-free or zero-waste bioenergy production method inclusive of a heterotrophic microalgae cultivation process.

Reference now should be made to the drawings, in which the same reference numerals are used throughout the different drawings to designate the same or similar components.

The present invention relates to a bioenergy production method with reduced carbon dioxide emissions and a minimized-waste or waste-free bioenergy production process; capable of providing optimal biomass treatment efficiency and bioenergy productivity, including a process for producing a bioalcohol and a biogas by subjecting a biomass, such as: herbaceous and woody plants, fruit pulp, freshwater and micro- and macroalgae, grains, aerobic and anaerobic sludge, saccharides, polyols and carbohydrates, to a combined process of a biosaccharification/alcohol fermentation including a biomass pretreatment process; and a process for producing a methane biogas, with a reduced level or elimination of carbon dioxide and hydrogen sulfide, via an autotrophic or mixotrophic algae cultivation process with a view to purifying the carbon dioxide and hydrogen sulfide contained in the biogas; wherein when the algae to be cultivated is microalgae, biodiesel is produced by subjecting the harvested microalgae to a biodiesel manufacturing process while recycling the resulting glycerol and saccharide-containing waste by-products to the biosaccharification/alcohol fermentation process; and when the algae to be cultivated is macroalgae the harvested macroalgae is recycled to the biosaccharification/alcohol fermentation process, in which FIGS. 1 and 2 provide relevant zero-waste bioenergy processes.

According to the present invention, the biomass 1 pretreatment process may include: mechanical treatment, heat treatment, microwave, ultrasonication, acid treatment, alkali treatment, steam explosion, electron beam irradiation, water steaming, etc.

The biosaccharification/alcohol fermentation process 2 may include a biosaccharification/alcohol fermentation process for producing bioethanol, or a biosaccharification/butanol fermentation process for producing biobutanol.

Additionally, the biosaccharification/alcohol fermentation process 2 may include a process for producing biobutanol by subjecting a liquid ethanol fermentation waste resulting from bioethanol production in the biosaccharification/alcohol fermentation process, or a solid biomass waste, or both of the liquid ethanol fermentation waste and the solid biomass waste as raw materials of the biosaccharification/butanol fermentation process. Meanwhile, part of the biomass-derived saccharide 20 generated from the biosaccharification process during the biosaccharification/alcohol fermentation process 2 may be supplied to the inside of the algae cultivation liquid (flow G) of the heterotrophic algae cultivation process 18 before being supplied to the bioalcohol fermentation process (FIG. 2).

According to the experimental results obtained by the inventors of the present invention, the liquid waste of bioethanol fermentation is an organic waste with a BOD ranging from 35,000 to 84,000 mg/L and having a high solid concentration; and the technology of efficiently treating the liquid waste of bioethanol was initially performed in the present invention. The present invention utilizing various organic materials present in the liquid waste of bioethanol as carbon sources for microorganisms is expected to be applicable in various manners to the fields of chemical raw materials and fuel production technologies, and is also expected to enhance the cost competitiveness of bioethanol.

Additionally, the liquid byproduct 11, including the solid biomass waste 10 generated while producing the bioalcohol 8 in the biosaccharification/alcohol fermentation process 2, and the fermentation liquid wastes generated while purifying bioethanol and biobutanol in their respective purification processes, generate a biogas 13 composed of methane, carbon dioxide, hydrogen sulfide, etc., while being passed through the anaerobic digestion process 3 (flow B), and eventually producing a purified methane biogas 6. The anaerobic digestion process 3 is performed in a continuous sequential process of hydrolysis, acidogenesis, and methanogenesis.

In the anaerobic digestion process 3, the organic solid materials with complex compositions are initially hydrolyzed into simple forms of soluble organic materials by fermentative bacteria, and then solid components such as carbohydrates, proteins, and lipids are respectively converted into monosaccharides, disaccharides, amino acids, fatty acids, etc. The hydrolysates are further decomposed into volatile fatty acids such as acetate, and the acidogenesis is performed by fermentative bacteria. During the acidogenesis, alcohol components such as ethanol and butanol may be produced in addition to the volatile fatty acids, and carbon dioxide and hydrogen may be concurrently produced. Of them, acetate, carbon dioxide and hydrogen may be used as substrates for methanogenesis, the final process of the anaerobic digestion. The methanogenesis process occurs in an absolute anaerobic condition by means of the bacterium *Archaea*.

The anaerobic digestion process 3 in the zero-waste bioenergy production process of the present invention employs byproducts generated during the fermentation process for alcohol production as raw materials. Among the byproducts, the solid components may exhibit carbohydrate deficiency because the carbohydrates of the solid components are mainly used in the previous step of the alcohol production process.

As an advantage of the present invention, in the anaerobic digestion process 3, proteins, lipids, and other insoluble materials present in the solid byproducts and high concentration carbon-containing organic materials contained in the liquid waste of alcohol fermentation are mainly converted into a methane biogas 6.

In an embodiment of the present invention, the anaerobic digestion reaction 3 employing the alcohol fermentation byproduct is performed using an upflow anaerobic sludge blanket (UASB) reactor, capable of maintaining the concentration of microorganisms high and enabling an easy solid-liquid separation by itself, so as to prevent the anaerobic digestion reaction from being inhibited by various components present in the fermentation liquid waste.

Additionally, in order to promote a smooth anaerobic digestion of the insoluble solid components, the above process may be performed by at least one or a combination thereof selected from the pretreatment methods consisting of: mechanical treatment, heat treatment, microwave, ultrasonication, acid treatment, alkali treatment, steam explosion, electron beam irradiation, and water steaming. According to the present invention, in order to utilize the biogas as an economical energy source, a biogas upgrading process to increase calorific value by increasing the purity of methane may be included.

The biogas upgrading process may adopt a method to initially remove the odorous $H_2S$ and at the same time reduce $CO_2$, a greenhouse gas in high concentrations. The method may be used in the representative $CO_2$ capture technology, applied for combustion flue gas of fossil fuels such as coal and petroleum. The method is a chemical absorption method using an alkanolamine-based absorbent such as mercaptoethylamine (MEA). The method is advantageous in that it enables a rapid $CO_2$ absorption; however it also requires a secondary $CO_2$ treatment after capture such as post-treatment of an absorption liquid, and also requires both high temperatures and energy input during the regeneration of the absorption liquid, and a corresponding large apparatus. Considering the disadvantages of the methods described above, the present invention adopted a biological $CO_2$ fixation technology using microalgae or 는 macroalgae.

In an embodiment of the present invention, the anaerobic digestion sludge 12 generated in the anaerobic digestion process 3 is converted into biochar 21 by pyrolysis. Meanwhile, the biogas 13 generated in the anaerobic digestion process is added into the lower part of the algae cultivation liquid of the autotrophic or mixotrophic algae cultivation process 4, thereby supplying carbon dioxide necessary for algal photosynthesis. Furthermore, the liquid waste 14 generated from the anaerobic digestion process is added into the respective algae cultivation liquid of the autotrophic or mixotrophic algae cultivation process 4 and the heterotrophic algae cultivation process 18, thereby supplying nitrogen and phosphorous to the algae cultivation liquid, respectively. In the present invention, the algae includes both the microalgae 15 and 19, and the macroalgae 16. Additionally, the hydrogen sulfide contained in the biogas 13 is dissolved in the algae cultivation liquid and treated as such. Here, the hydrogen sulfide oxidizing agent used in the present invention may be at least one selected from the group consisting of: Fe(III) EDTA, a ferric salt exclusive of Fe(III III) EDTA, oxygen ($O_2$), hydrogen peroxide ($H_2O_2$), chlorine ($Cl_2$), sodium hypochlorite (NaOCl), monochloroamine ($NH_2Cl$), or ozone ($O_3$). In Example 2 of the present invention, when the concentration of Fe(III) EDTA added into the algae cultivation liquid was in the range of from 0 to 4 mM the $CO_2$ removal rate was in the range of from 35 to 40%, and the $H_2S$ removal rate was consistently close to 100%. Accordingly, it was confirmed that when the hydrogen sulfide load in the biogas exceeded the critical limit, the excess hydrogen sulfide could be oxidized into free sulfur (S°) by maintaining the added concentration of Fe(III) EDTA at 4 mM or below. In Example 2 of the present invention, the biogas was converted into a methane biogas 6. Furthermore, when the algae is microalgae 15 and 19, biodiesel 7 may be produced by adding the microalgae 15 and 19 harvested from the algae cultivation processes 4 and 18 into the biodiesel production process 5. In the present invention, the microalgae 15 and 19 may accumulate about from 30 to 50% of lipid oil per dry weight by controlling their cultivation conditions, and some algal species produce up to 70% oil.

According to the present invention, the defatted cells 17 of the microalgae after fat extraction for biodiesel production contained carbohydrates and proteins, in which carbohydrate content was usually in the range of from 45 to 50%. Therefore, the carbohydrates were used as a raw material for the alcohol fermentation process 2 after an appropriate hydrolysis.

According to the present invention, high-concentration glycerol 9, in the range of from 5 to 20% (w/v) relative to the amount of the biodiesel production (E), is produced as a byproduct (flow D) in the biodiesel production process 5.

Accordingly, in the present invention, liquid glycerol 9, a byproduct generated from the biodiesel production process 5, is either supplied to the algae cultivation liquid of the liquid glycerol 9 (flow F) or recycled to the biosaccharification/alcohol fermentation process (flow C), whereas the saccharide-containing solid waste, a byproduct of the biodiesel production process 5, is recycled to the biomass pretreatment process of the biosaccharification/alcohol fermentation process 2.

According to the present invention, when the algae in the algae cultivation process 4 is macroalgae, upon harvesting the macroalgae, the harvested microalgae 16 is recycled into the biomass pretreatment process of the biosaccharification/alcohol fermentation process 2, whereas the microalgae 19 harvested from the heterotrophic microalgae cultivation process 18 is recycled into the biodiesel production process 5, either simultaneously with or separately (flow H) apart from the microalgae 15 harvested from the autotrophic or mixotrophic cultivation process 4.

Accordingly, the present invention provides a bioenergy production process with reduced carbon dioxide emissions; and a minimized-waste or waste-free bioenergy production process capable of providing optimal biomass treatment efficiency and bioenergy productivity while overcoming the issue of carbon dioxide emissions. Carbon dioxide being a representative greenhouse gas contributing to the global warming.

Specific structural and functional descriptions of embodiments of the major processes in each step of the present invention are disclosed herein below. However, the embodiments of the present invention are disclosed only for illustrative purposes and should not be construed as limiting the scope of the present invention.

EXAMPLE 1

Experiment on a Zero-Waste Bioenergy Production Process for Calculation of Bioenergy Productivity of the Present Invention A process simulation regarding the amount of bioenergy production according to its type using fruit byproducts as a raw material was performed by applying the zero-waste bioenergy production process of the present invention based on the mass balance equation. In this Example, fruit byproducts in the amount of 9,000 tons collected over the course of one calendar year were used. The stoichiometric coefficients applied were: a fruit byproducts' carbohydrate content of 80%; a carbohydrate content of the biomass waste, generated in the biodiesel production process, of 30%; a bioethanol yield per carbohydrate of 0.45; a bioethanol yield per glycerol waste of 0.45; a butanol production rate, relative to that of ethanol, of 5%; a biogas yield per unit of biomass in the anaerobic digestion process of 0.3; concentrations of carbon dioxide and methane in the biogas of 40% and 60% respectively; a yield of microalgae production using carbon dioxide in the biogas of 0.25; a yield of biodiesel production per unit of algal biomass of 0.4, and a rate of the amount of glycerol waste production relative to that of biodiesel production of 0.1.

The simulation revealed that, when the fruit byproducts in the amount of 9,000 tons based upon cumulative annual collection were used as a raw material, the potential annual production quantities as calculated were: 3,245 tons for bioenergy, 162 tons for biobutanol, 328 tons for purified biogas, and 22 tons for biodiesel, as shown in Table 1 below.

According to Example 1 of the present invention, a high bioenergy production rate (tons/year) of 41.7% or higher relative to the raw material collection rate (tons/year) was achieved. In Example 1, the anaerobic sludge generated in the anaerobic digestion process recycled into the biomass pretreatment process was not considered. Meanwhile, the intermediate products, being circulated within the entire process, were introduced to the subsequent unit process, respectively, and the intermediate products generated from the biodiesel production process were recycled to the biosaccharification/alcohol fermentation process.

TABLE 1

Results of simulation of zero-waste bioenergy production process of the present invention

| Unit process | Material to be added | | Intermediate product | | Amount of bioenergy production | |
|---|---|---|---|---|---|---|
| Biosaccharification/ alcohol fermentation process | Fruit byproduct | 9,000 | Biomass waste | 1,823 | Bioethanol | 3,245 |
| | Biomass waste | 33 | | | Biobutanol | 162 |
| | Glycerol waste | 2 | | | | |
| Anaerobic digestion process | Biomass waste | 1,823 | Biogas | 547 | | |
| Algae cultivation process | Biogas | 547 | Microalgae | 55 | Purified biogas | 328 |
| Biodiesel production process | Microalgae | 55 | Biomass waste | 33 | Biodiesel | 22 |
| | | | Glycerol waste | 2 | | |

EXAMPLE 2

Removal of Carbon Dioxide and Hydrogen Sulfide from Microalgae Cultivator

Figure 3A:
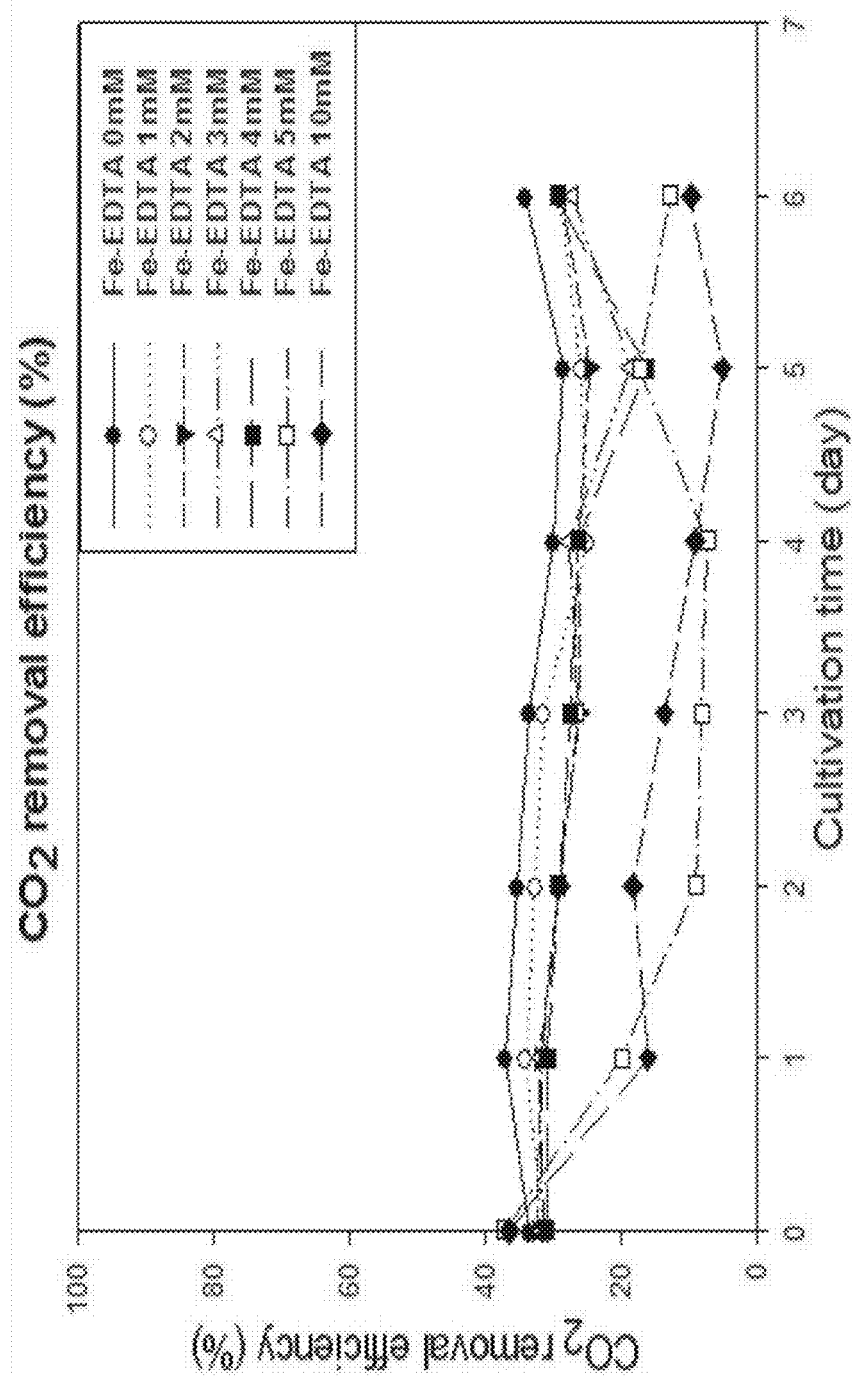
FIG. 3A is a graph showing the change in $CO_2$ concentration due to the addition of an Fe(III) EDTA absorbent during the microalgae cultivation.
Figure 3B:
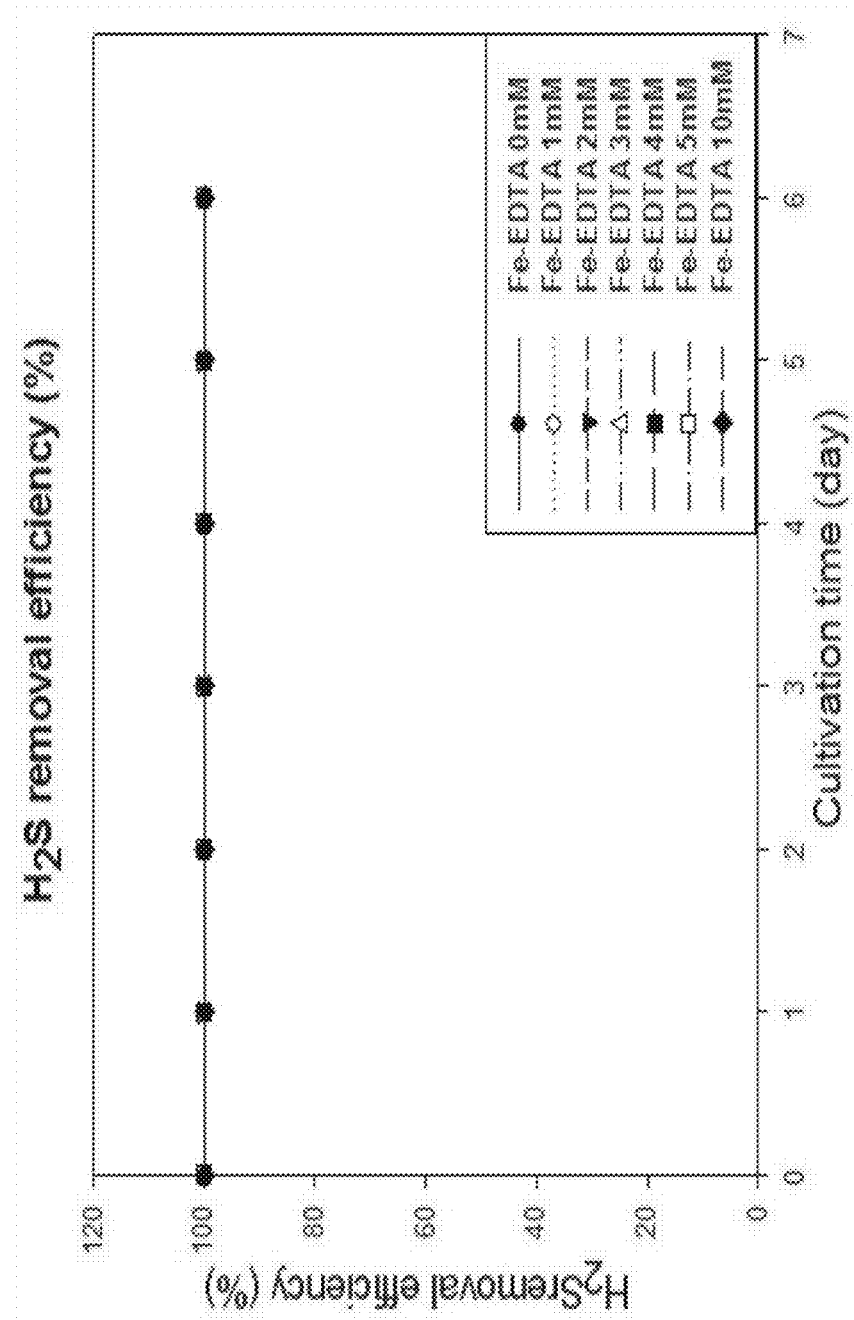
FIG. 3B is a graph showing the change in $H_2S$ concentration due to the addition of an Fe(III) EDTA absorbent during the microalgae cultivation.
Figure 3C:
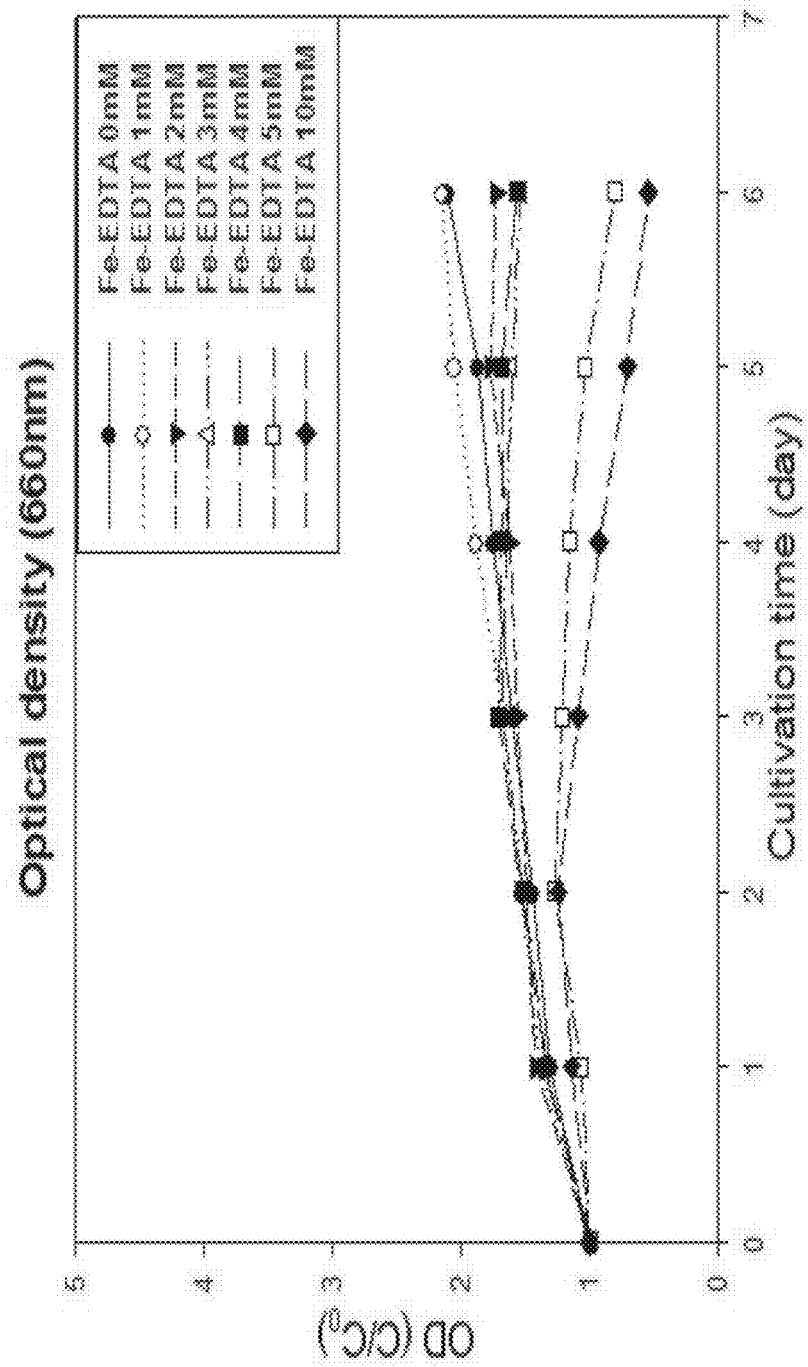
FIG. 3C is a graph showing the change in optical density according to cell concentration during the microalgae cultivation.
Figure 3D:
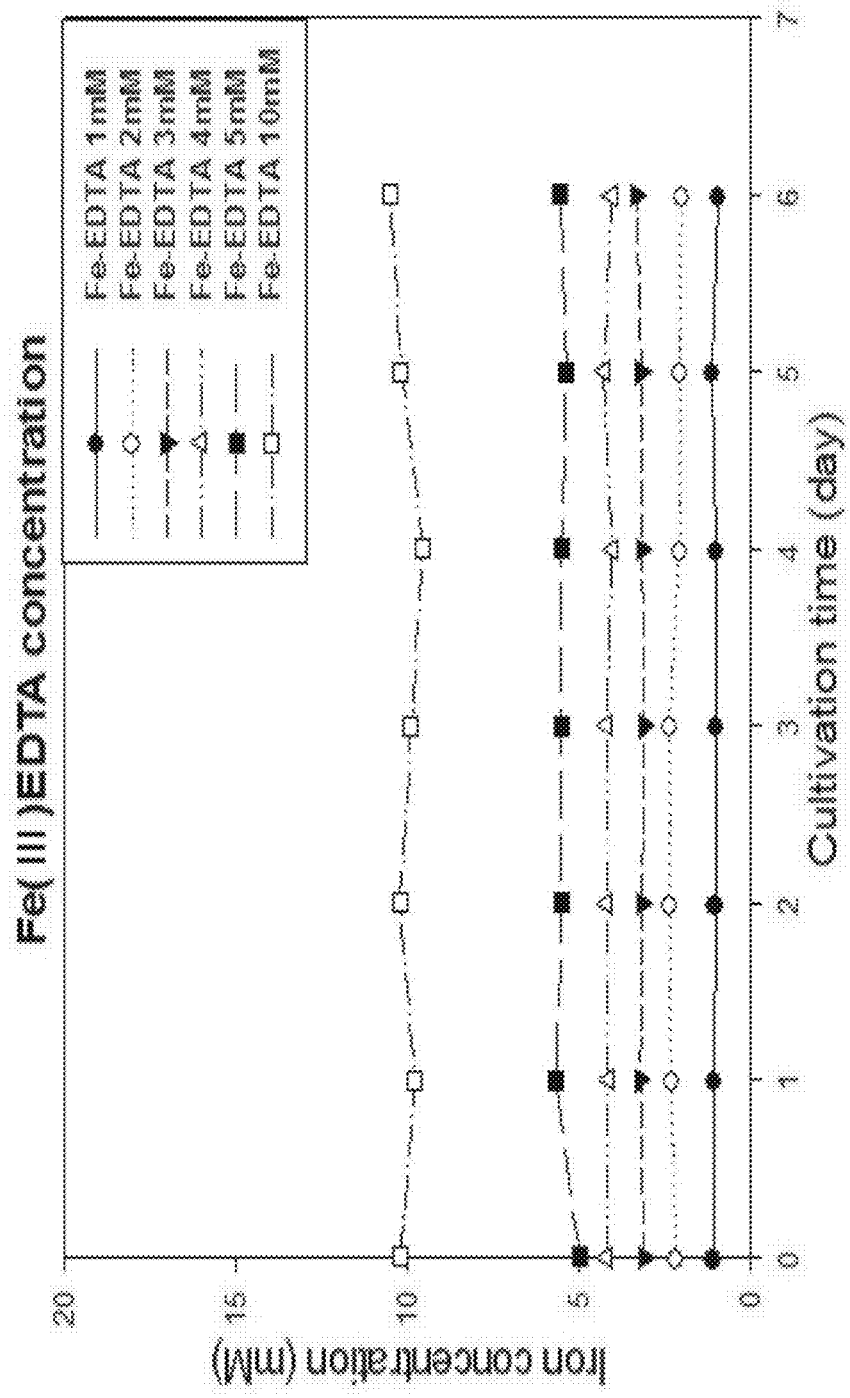
FIG. 3D is a graph showing the change in Fe(III) concentration according to cell concentration during the microalgae cultivation.

Microalgae *Scenedesmus accuminatus* AG10316 was cultivated in an Fe(III) EDTA-containing photobioreactor with a supply of 5% $CO_2$ and 0.01% $H_2S$. Fe(III) EDTA was used as an absorbent for $H_2S$ oxidation. For the control group, all cultivation conditions were the same except for the presence of microalgae in place of the macroalgae of Example 1. The experimental results revealed that $H_2S$ was precipitated as free sulfur (S°), and $CO_2$, being microalgae's carbon source, was fixed in the form of biomass via photosynthesis. The experimental results also revealed: the rate of $CO_2$ removal according to the concentration of added Fe(III) EDTA (FIG. 3A), the rate of $H_2S$ removal (FIG. 3B), the change in optical density according to cell concentration (FIG. 3C), and the change in Fe(III) concentration according to cell concentration (FIG. 3D).

In this Example, the Fe(III) EDTA concentration being added in the range of from 0 to 4 mM showed a $CO_2$ removal rate of from 35 to 40%, and an almost constant $H_2S$ removal rate close to 100%. The cell concentration, increased over time within the Fe(III) EDTA concentration ranging from 0 to 4 mM; thus confirming that simultaneous removal of $CO_2$ and $H_2S$ is possible. Additionally, it was speculated that the Fe(III) concentration was maintained at a constant level without any variation in this Example because Fe(II) was oxidized to Fe(III) by the oxygen generated from algal photosynthesis and recycled thereafter.

EXAMPLE 3

Production of Bioalcohol from Glycerol

The ethanol-producing yeast strain, *Saccharomyces cerevisiae* KCTC 7296, was purchased from the Biological Resource Center (BRC) of Korea Research Institute of Bioscience and Biotechnology (KRIBB). The yeast strain was cultured in a GPY medium (see Table 2) kept at 30° C. aerobically at a rate of 130 rpm, and then stored along with 25% glycerol in a deep freeze at −72° C., and used as a testing material of the present invention.

TABLE 2

Composition of GPY medium for *S. cerevisiae* KCTC 7296

| Component | g/L |
|---|---|
| Glucose | 40 |
| Peptone | 5 |
| Yeast extract | 5 |

The composition of the ethanol-producing medium for *S. cerevisiae* KCTC 7296 contained 150 g of glucose, 1.95 g of $NH_4Cl$, 0.12 g of $MgSO_4 7H_2O$, 0.06 g of CaCl2, and 8.5 g of yeast extract. For culturing the *S. cerevisiae* KCTC 7296 frozen in 25% glycerol as a test material, it was inoculated onto the GPY agar medium, incubated at 30° C. for 23 days, activated, and then single colonies were inoculated onto 100 mL of liquid GPY medium, and incubated at 30° C. under 130 rpm for 1.5 days. The entire culture medium was centrifuged and the resulting microorganism pellet was washed once with 0.85% NaCl solution, and suspended in 10 mL of 0.85% NaCl solution. The ethanol production was performed in two 10 L stirred-vessel fermenters (Fermentec Co., Ltd., Korea), and the real working volume was was 7

L (a total of 14 L). When culturing the microorganism in a flask the culturing conditions were set at 30° C. and 130 rpm; whereas when cultured in a fermenter, the culturing conditions were set at 30° C. and 300 rpm without pH adjustment. The upper portions of the flask and the fermenter were respectively sealed with a sponge culture cap allowing a free passage for gases.

The results revealed that, after 50.5 hours of reaction, 60.1 g/L of ethanol was produced along with 1 g/L of acetic acid and 1.9 g/L of 2,3-butanediol as byproducts. The ethanol yield was 0.4 g-ethanol/g-glucose, about 80% of the theoretical yield.

As described above, the present invention provides an.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for producing multiple bioenergy products, said method comprising:
    a) providing a first biomass,
    b) subjecting the first biomass to a pretreatment process;
    c) subjecting the pretreated biomass to a combined biosaccharification/alcohol fermentation process to produce a bioalcohol, a liquid byproduct, and a solid biomass waste;
        c1) further subjecting the bioalcohol to bioalcohol purification to produce a bioalcohol energy product and a liquid waste;
        c2) further subjecting the liquid byproduct liquid waste and solid biomass waste to an anaerobic digestion process to produce an anaerobic sludge and a biogas comprising methane, carbon dioxide, and hydrogen sulfide;
            c2i) further recycling at least a portion of the anaerobic sludge to the biomass pretreatment process of step b);
    d) purifying a methane energy product by introducing the biogas into an algae cultivation liquid in an algae cultivation process, wherein algae in the algae cultivation process are autotrophic or mixotrophic, and utilize the carbon dioxide for photosynthesis and absorb the hydrogen sulfide, and the algae cultivation process provides a second biomass;
        d1) further recycling the second biomass to the combined biosaccharification/alcohol fermentation process of step c);
    e) optionally, when the algae are microalgae, subjecting the microalgae to a biodiesel manufacturing process to produce a biodiesel energy product, a liquid glycerol byproduct, and a saccharide-containing solid waste;
        e1) optionally, further recycling the liquid glycerol byproduct to the biomass pretreatment process of step b);
        e2) optionally, further recycling the saccharide-containing solid waste to the combined biosaccharification/alcohol fermentation process of step c); and
    f) optionally, when the algae are macroalgae, further recycling harvested macroalgae to the biomass pretreatment process of step b).

2. The method of claim 1, wherein the biomass pretreatment process is performed by one or a combination thereof selected from the group consisting of mechanical treatment, heat treatment, microwave, ultrasonication, acid treatment, alkali treatment, steam explosion, electron beam irradiation, and water steaming.

3. The method of claim 1, wherein the first biomass is one or a combination thereof selected from the group consisting of: herbaceous and woody plants, fruit pulp, freshwater and sea algae, grains, aerobic and anaerobic sludge, saccharides, polyols and carbohydrates.

4. The method of claim 1, wherein the anaerobic digestion process comprises a pretreatment of a non-biodegradable solid biomass waste.

5. The method of claim 1, wherein the anaerobic digestion process is performed using an upflow anaerobic sludge blanket (UASB) reactor.

6. The method according to claim 1, wherein the anaerobic digestion process supplies nitrogen and phosphorous to the algae cultivation liquid by adding a liquid waste containing nitrogen and phosphorous to the algae cultivation process.

7. The method according to claim 1, wherein the bioalcohol energy product produced during the combined biosaccharification/alcohol fermentation process is ethanol or butanol.

8. The method of claim 1, wherein a portion of the anaerobic sludge not recycled to the biomass pretreatment process is manufactured into a biochar via pyrolysis.

9. The method of claim 1, wherein the algae cultivation liquid is further combined with at least one oxidizing agent to promote the absorption of the hydrogen sulfide during the algae cultivation process,
    wherein said at least one oxidizing agent is Fe(III) EDTA, a ferric salt exclusive of Fe(III) EDTA, oxygen (O2), hydrogen peroxide (H2O2), chlorine (Cl2), sodium hypochlorite (NaOCl), monochloroamine (NH2Cl) or ozone (O3).

10. The method of claim 1, wherein the liquid byproduct has a biological oxygen demand (BOD) concentration in the range of from $10^4$ to $10^5$ mg/L.

11. The method of claim 1, wherein the microalgae contains at least 30% lipid oil per dry weight.

12. The method of claim 1, wherein the liquid glycerol byproduct concentration is in the range of from 5 to 20% w/v relative to the amount of the biodiesel produced from the biodiesel manufacturing process.

13. The method of claim 1, wherein the saccharide-containing solid waste contains carbohydrate in the range of from 45 to 50%.

14. The method of claim 4, wherein the pretreatment of the non-biodegradable solid biomass waste is performed by one or a combination thereof selected from the group consisting of mechanical treatment, heat treatment, microwave, ultrasonication, acid treatment, alkali treatment, steam explosion, electron beam irradiation, and water steaming.

15. The method of claim 9, wherein the oxidizing agent is Fe(III) EDTA, and the Fe(III) EDTA concentration in the algae cultivation liquid is maintained at 4 mM or less.

16. The method of claim 1, the method further comprising a heterotrophic algae cultivation process performed after any one of the anaerobic digestion process of c2), the algae cultivation process of d), the recycling of the at least a portion of the liquid glycerol byproduct of c1), and the recycling of the at least a portion of the saccharide-containing solid waste of e2).

17. The method of claim 16, wherein the heterotrophic algae cultivation process further comprises supplying a portion of the liquid glycerol byproduct not recycled to the combined biosaccharification/alcohol fermentation process into a heterotrophic algae cultivation liquid in the heterotrophic algae cultivation process.

18. The method according to claim 16, wherein the heterotrophic algae cultivation process further comprises supplying a portion of the saccharide-containing solid waste not recycled to the biomass pretreatment process into a heterotrophic algae cultivation liquid in the heterotrophic algae cultivation process.

19. The method according to claim 16, wherein a liquid waste from the anaerobic digestion process is supplied to the heterotrophic algae cultivation process thereby supplying nitrogen and phosphorous to a heterotrophic algae cultivation liquid in the heterotrophic algae cultivation process.

* * * * *